United States Patent [19]

Giger et al.

[11] Patent Number: 5,510,353
[45] Date of Patent: Apr. 23, 1996

[54] CERTAIN AMINOGUANIDINE COMPOUNDS, PHARMACEUTICAL COMPOSITIONS CONTAINING THEM AND THEIR USE IN TREATING GASTROINTESTINAL MOTILITY DISORDERS AND DISORDERS ASSOCIATED WITH CEPHALIC PAIN

[75] Inventors: Rudolf K. A. Giger, Muttenz, Switzerland; Henri Mattes, Brunstadt, France

[73] Assignee: Sandoz Ltd., Basel, Switzerland

[21] Appl. No.: 370,038

[22] Filed: Jan. 9, 1995

Related U.S. Application Data

[63] Continuation of Ser. No. 125,090, Sep. 21, 1993, abandoned, which is a continuation of Ser. No. 17,722, Feb. 16, 1993, abandoned, which is a continuation of Ser. No. 855,184, Mar. 20, 1992, abandoned.

[30] Foreign Application Priority Data

Mar. 22, 1991 [GB] United Kingdom ............ 9106179
Apr. 15, 1991 [GB] United Kingdom ............ 9107927

[51] Int. Cl.$^6$ .............. A61K 31/40; A61K 31/425; C07D 209/14; C07D 417/12
[52] U.S. Cl. .............. 514/300; 514/387; 514/226.8; 514/227.2; 514/269; 514/272; 514/415; 514/339; 514/392; 514/323; 514/255; 514/414; 544/337; 544/54; 544/55; 544/405; 546/201; 546/273; 546/113; 548/305; 548/312.1; 548/496; 548/505
[58] Field of Search .................. 514/300, 387, 514/415, 226.8, 227.2, 269, 272, 255, 339, 392, 323; 546/113, 201, 273; 548/305, 496, 505, 312.1; 544/54, 55, 337, 405

[56] References Cited

U.S. PATENT DOCUMENTS

| | | | |
|---|---|---|---|
| 2,855,398 | 10/1958 | Voegtli | 514/415 |
| 3,317,560 | 5/1967 | Claassen | 514/415 |

FOREIGN PATENT DOCUMENTS

| | | |
|---|---|---|
| 488897 | 6/1992 | European Pat. Off. |
| 842325 | 7/1960 | United Kingdom |
| 842322 | 7/1960 | United Kingdom |
| 842323 | 7/1960 | United Kingdom |
| 842324 | 7/1960 | United Kingdom |
| 92/03132 | 3/1992 | WIPO |

*Primary Examiner*—Jacqueline Haley
*Attorney, Agent, or Firm*—Robert S. Honor; Melvyn M. Kassenoff; Joseph J. Borovian

[57] ABSTRACT

Compounds of formula

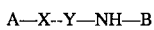

wherein A is derived from optionally substituted benzothiophene, indole, 4-aza-and 7-aza-benzothiophene or-indole, A bearing in position 5 hydrogen, halogen, optionally substituted alkyl, hydroxy, nitro, amino, alkylamino, acylamino, alkoxycarbonyl, sulfamoyl, cyano, trimethylsilyl, carboxy, carbamoyl, phosphate, oxycarbamoyl, heterocyclic radical or ether or ester group, X-Y is —$CR_8$=N— or $CH(R_8)$—NH— wherein $R_8$ is -H or alkyl and attached at position 3 of A, and B is a heterocyclic radical or a residue

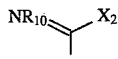

wherein $R_{10}$ is H, optionally substituted alkyl, cycloalkyl, aryl, adamantyl, acyl or carbamoyl and $X_2$ is alkylthio or $NR_3R_{10}$ wherein $R_3$ is H or alkyl or $R_3$ and $R_{10}$ together with the nitrogen atom to which they are attached form a heterocyclic radical, in free form or in salt form, have pharmacological activity, e.g. for treating gastrointestinal disorders.

17 Claims, No Drawings

CERTAIN AMINOGUANIDINE COMPOUNDS, PHARMACEUTICAL COMPOSITIONS CONTAINING THEM AND THEIR USE IN TREATING GASTROINTESTINAL MOTILITY DISORDERS AND DISORDERS ASSOCIATED WITH CEPHALIC PAIN

This is a continuation of application Ser. No. 08/125,090, filed Sep. 21, 1993, now abandoned, which in turn is a continuation of application Ser. No. 08/017,722, filed Feb. 16, 1993, now abandoned which in turn is a continuation of application Ser. No. 07/855,184, filed Mar 20, 1992, now abandoned.

The present invention relates to aminoguanidines having pharmaceutical utility, processes for their production, pharmaceutical compositions comprising them and their use as pharmaceuticals.

More particularly the present invention provides a compound of formula I,

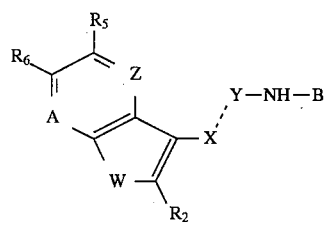

wherein

W is S or —$NR_1$— wherein $R_1$ is hydrogen, $C_{1-6}$alkyl or acyl, $R_2$ is hydrogen, halogen or $C_{1-6}$alkyl, $R_5$ is hydrogen; halogen; $C_{1-6}$alkyl; hydroxy; nitro; amino; $C_{1-4}$alkylamino; acylamino; $C_{2-6}$alkoxycarbonyl; $SO_2NR_aR_b$ wherein each of $R_a$ and $R_b$ independently is hydrogen or $C_{1-6}$alkyl; cyano; or trimethylsilyl;

or, when A is —$CR_7$=, $R_5$ is also $C_{1-6}$alkyl substituted by —$SO_2$-$C_{1-6}$alkyl, —$SO_2NR_aR_b$, —$CONR_aR_b$, —NH—$SO_2$-$C_{1-6}$alkyl, —N($C_{1-6}$alkyl)—$SO_2$-($C_{1-6}$alkyl), —$NR_aR'_b$ wherein $R'_b$ is hydrogen, $C_{1-6}$alkyl, $C_{3-7}$cycloalkyl, $C_{3-6}$alkenyl, phenyl or phenyl-$C_{1-3}$alkyl wherein the phenyl ring is optionally substituted, $C_{2-6}$alkoxycarbonyl, —PO($C_{1-4}$alkyl)$_2$ or a heterocyclic radical; carboxy; $CONR_aR_b$; —PO($C_{1-4}$alkyl)$_2$; $OCONR_cR_d$, wherein each of $R_c$ and $R_d$ independently is $C_{1-6}$alkyl; or a heterocyclic radical, $R_6$ is hydrogen or, when $R_5$ is OH, $R_6$ is hydrogen or halogen, Z is —$CR_4$= wherein $R_4$ is hydrogen, halogen, hydroxy or $C_{1-6}$alkyl or, when $R_5$ is hydrogen or hydroxy, Z is also —N=, A is —N= or —$CR_7$= wherein $R_7$ is hydrogen, halogen, $C_{1-6}$alkyl or $C_{1-6}$alkoxy, or $R_1$ and $R_7$ together represent —$(CH_2)_m$— or —$X_3(CH_2)_p$— wherein m is 2, 3 or 4, p is 2 or 3 and $X_3$ is O, S or —N($C_{1-6}$alkyl)—, $X_3$ being attached to the 6-membered ring, X-Y is —$CR_8$=N— or —$CH(R_8)$—NH— wherein $R_8$ is hydrogen or $C_{1-6}$alkyl, and B is a radical of formula (a) or (b),

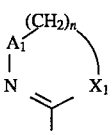

wherein n is 1 or 2, $A_1$ is C=O or $CH_2$, $X_1$ is S, $NR_{11}$ or $CR_{12}R_{13}$, wherein $R_{11}$ is hydrogen or acyl, each of $R_{12}$ and $R_{13}$ independently is hydrogen, $C_{1-4}$alkyl or $C_{5-7}$cycloalkyl, $R_{10}$ is hydrogen; $C_{1-12}$alkyl; $C_{1-6}$alkyl substituted by hydroxy, aryl, aryloxy, adamantyl, a heterocyclic radical, —$NR_{15}$—CO—$R_{16}$ or —NH—$SO_2$—aryl; $C_{5-7}$cycloalkyl; aryl; adamantyl; acyl; or —$CONHR_{14}$, wherein $R_{14}$ is $C_{1-10}$alkyl, $C_{5-7}$cycloalkyl, $C_{5-7}$cycloalkyl-$C_{1-4}$alkyl, aryl, aryl$C_{1-4}$alkyl or a heterocyclic radical, $R_{15}$ is hydrogen or $C_{1-4}$alkyl, and $R_{16}$ is $C_{1-6}$alkyl, $C_{5-7}$cycloalkyl, $C_{5-7}$cycloalkyl-$C_{1-4}$alkyl, aryl or aryl$C_{1-4}$alkyl, and $X_2$ is —$SR_{20}$ or —$NR_3R'_{10}$ wherein $R_{20}$ is $C_{1-6}$alkyl, $R_3$ is hydrogen or $C_{1-6}$alkyl and $R'_{10}$ has one of the significances given for $R_{10}$ above, or $R_3$ and $R'_{10}$ together with the nitrogen atom to which they are attached form a 5-, 6- or 7-membered saturated, aromatic or non aromatically unsaturated heterocycle which may comprise a further heteroatom selected from N, S and O and which may be further condensed to a benzene ring, provided that i) when B is a radical of formula (b), only one of $R_{10}$ and $R'_{10}$ can be other than hydrogen and $X_2$ can be —$SR_{20}$ only when $R_{10}$ is hydrogen, and ii) $R_5$ is other than hydrogen when B is a radical

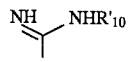

wherein $R'_{10}$ is 4-methylphenyl as aryl, each of Z and A is —CH=, W is —NH—, $R_2$ and $R_6$ are each hydrogen and X--Y is CH=N—and a physiologically-hydrolyzable and -acceptable ether or ester thereof when $R_5$ is hydroxy, in free form or in salt form.

By the term "physiologically-hydrolyzable and-acceptable ethers and esters" as applied to the compounds of formula I when $R_5$ is hydroxy, is meant ethers in which $R_5$ is etherified and esters in which $R_5$ is esterified and which are hydrolyzable under physiological conditions to yield an alcohol or acid which is physiologically acceptable, i.e. which is non-toxic at the desired dosage levels.

Examples of ether groups as $R_5$ include e.g. $C_{1-6}$alkoxy; $C_{1-6}$alkoxy substituted by hydroxy, $C_{1-4}$alkoxy, acyloxy, $NR_aR'_b$, $CONR_aR_b$ or $CSNR_aR_b$ wherein $R_a$, $R_b$ and $R'_b$ are as defined above; and $C_{2-6}$alkenyloxy. Z may also be=N— when $R_5$ is an ether group.

Examples of ester groups as $R_5$ include e.g. acyloxy and pyridyl-carbonyloxy. When $R_5$ is an ester group, it is preferably pyridyl-carbonyloxy. When A is —$CR_7$=, $R_5$ as an ester group is preferably acyloxy or pyridyl-carbonyloxy.

In the compounds of formula I, alkyl groups and moieties may be branched or straight chain. When $R_5$, $R_{10}$ or $R'_{10}$ are substituted alkyl, the substituent is preferably located at the end of the alkyl chain.

By halogen is preferably meant fluorine or chlorine.

When $R_5$ is hydroxy-substituted $C_{1-6}$alkoxy, it may also be alkoxy polysubstituted with hydroxy, e.g. 2,3-dihydroxypropoxy.

Aryl is preferably phenyl or naphthyl, preferably phenyl, and may be substituted. Aryl$C_{1-4}$alkyl is preferably phenyl-$C_{1-4}$alkyl, e.g. benzyl or phenethyl, and may be substituted on the phenyl ring. Aryloxy is preferably phenoxy, and may be substituted. Aryl$C_{1-6}$alkoxy is e.g. benzyloxy, and may be substituted on the phenyl ring. When aryl or the aryl moiety are substituted, they may be mono-or polysubstituted, for example by halogen, $C_{1-4}$alkyl or $C_{1-6}$ alkoxy. Examples are e.g. phenyl or phenyl moiety mono-or disubstituted by chlorine, methyl or methoxy.

Acyl groups or acyl moieties in acyloxy are preferably RCO, where R is $C_{1-10}$alkyl, $C_{2-10}$alkenyl, $C_{5-7}$cycloalkyl or aryl, preferably $C_{1-10}$alkyl.

When each of $R_1$ and $R_{11}$ independently is acyl, it is preferably R'CO, where R'is $C_{1-6}$alkyl, phenyl or phenyl$C_{1-4}$alkyl, particularly $C_{1-6}$alkyl. When $R_{10}$ is acyl, it is preferably R"CO, where R" is $C_{1-10}$alkyl, phenyl or phenyl$C_{1-4}$alkyl, particularly $C_{1-10}$ alkyl. When $R_5$ is acyloxy, it is preferably R'—CO—O—.

Heterocyclic radical as $R_5$ is e.g. a radical derived from oxazole, thiazole, isoxazole, oxadiazole or thiadiazole. When $R_5$ is or comprises a heterocyclic radical, such is preferably a radical of formula (α)

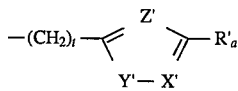 (α)

wherein t is 0,1,2 or 3

$R'_a$ is hydrogen or $C_{1-6}$ alkyl

X' is N or CH

Y' is O, and

Z' is N.

Heterocyclic radical as $R_{10}$, $R'_{10}$ or as formed together by $R_3$ and $R'_{10}$ and the nitrogen atom to which they are attached is preferably a radical derived from a 5- or 6-membered saturated, aromatic or unsaturated heterocycle, optionally fused with a benzene ring, e.g. pyridine, imidazole, benzimidazole, pyrrolidine, pyrrolidone, piperidine, pyrazine or perhydroindole or a radical of formula (c), (d) or (e)

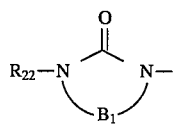 (c)

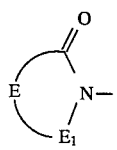 (d)

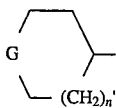 (e)

wherein $R_{22}$ is hydrogen or $C_{1-4}$alkyl, $B_1$ is —CH$_2$CH$_2$—, —COCH$_2$— or —(CH$_2$)$_3$—in which one or two H thereof can be replaced by $C_{1-4}$alkyl, or 1,2-phenylene, E is —CH$_2$CH$_2$—, —CH$_2$N(R$_{17}$)— or —(CH$_2$)$_3$—in which one or two H thereof can be replaced by $C_{1-6}$alkyl, or 1,2-phenylene, $E_1$ is CO or CH$_2$, $R_{17}$ is hydrogen or $C_{1-4}$alkyl, G is CO, —CHCOOR$_{18}$, —CHCOR$_{19}$, 5,5-dimethyl-1,3-dioxan-2-ylidene or 1,3-dioxolan-2-ylidene, wherein $R_{18}$ is hydrogen or $C_{1-6}$alkyl and $R_{19}$ is $C_{1-6}$alkyl, and n' is 0 or 1.

The heterocyclic radical may be further substituted, e.g. by halogen.

Examples of alkyl substituted by a heterocyclic radical are e.g. 2-(2-pyrrolidone-1-yl)-ethyl, and 3-benzimidazolyl-propyl. When B is a radical (b) wherein $R_{10}$ is hydrogen and $X_2$ is NR$_3$R'$_{10}$, preferably $R_3$ and R'$_{10}$ are not both hydrogen.

In the compounds of formula I, the following significances are preferred either individually or in any combination or sub-combination:

1. W is S, —NH—, —NCH$_3$— or —NC$_2$H$_5$—. More preferably W is NH.
2. $R_2$ is H, CH$_3$, Cl or Br. More preferably $R_2$ is H.
3. Z is —CR$_4$=.
4. $R_4$ is hydrogen or $C_{1-4}$alkyl, preferably hydrogen or methyl.
5. Z is —N=, $R_5$ is hydroxy or $C_{1-4}$ alkoxy and A is —CR$_7$=.
6. $R_5$ is hydrogen; hydroxy; or $C_{1-6}$alkoxy; or when A is —CR$_7$=, $R_5$ is also $C_{1-6}$alkyl substituted by —SO$_2$—$C_{1-6}$alkyl, —SO$_2$NR$_a$R$_b$, —CONR$_a$R$_b$, —NH—SO$_2$—$C_{1-6}$alkyl, —N($C_{1-6}$alkyl)—SO$_2$—$C_{1-6}$alkyl or —PO($C_{1-4}$alkyl)$_2$; acyloxy; carboxy; CONR$_a$R$_b$; —PO($C_{1-4}$alkyl)$_2$; or OCONR$_c$R$_d$.
7. A is —CR$_7$=.
8. $R_7$ is H or CH$_3$.
9. X-Y is —CR$_8$=N—.
10. $R_8$ is H or CH$_3$.
11. B is a radical of formula (a), preferably a radical of formula (a) wherein $X_1$ is —NH—.
12. B is a radical of formula (b).
13. $R_{10}$ is hydrogen.
14. $X_2$ is NR$_3$R'$_{10}$.
15. $R_3$ is hydrogen or $C_{1-4}$alkyl.
16. R'$_{10}$ is hydrogen, $C_{1-12}$alkyl, R"CO, CONHR$_{14}$, —(CH$_2$)$_{1-5}$—NH—CO—R$_{16}$ or $C_{1-6}$alkyl substituted in ω by aryl, a radical of formula (d) or benzimidazolyl. More preferably R'$_{10}$ is $C_{1-12}$alkyl.
17. $R_3$ and R'$_{10}$ together with the nitrogen atom to which they are attached form a 5-, 6- or 7- membered saturated, aromatic or non aromatically unsaturated heterocyclic group which may comprise a further heteroatom selected from N, S and O and which may be further condensed to a benzene ring. More preferably $R_3$ and R'$_{10}$ together with the nitrogen atom to which they are attached are piperidino or perhydroindolyl.
18. The radical of formula (d) is

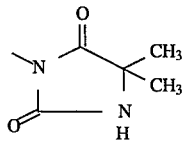

One group of compounds in accordance with the invention is a group of compounds of formula I wherein W, $R_2$, A, X-Y and B are as defined above, Z is —$CR_4$= as defined above and $R_5$ is hydrogen; $C_{1-6}$alkyl; hydroxy; $C_{1-6}$alkoxy; $C_{1-6}$alkoxy substituted by hydroxy, $C_{1-4}$alkoxy, acyloxy—, $NR_aR'_b$, $CONR_aR_b$ or $CSNR_aR_b$ wherein each of $R_a$ and $R_b$ independently is hydrogen or $C_{1-6}$alkyl and $R'_b$ is hydrogen, $C_{1-6}$alkyl, $C_{3-7}$cycloalkyl, $C_{3-6}$alkenyl, phenyl or phenyl-$C_{1-3}$alkyl wherein the phenyl ring is optionally substituted;

$C_{2-6}$alkenyloxy; pyridyl-carbonyloxy; nitro; amino; $C_{1-4}$alkylamino; acylamino; $C_{2-6}$alkoxycarbonyl; $SO_2NR_aR_b$;

cyano; or trimethylsilyl;

or, when A is —$CR_7$=, $R_5$ is also $C_{1-6}$alkyl substituted by —$SO_2$—$C_{1-6}$alkyl, —$SO_2NR_aR_b$, —$CONR_aR_b$, —NH—$SO_2$—$C_{1-6}$alkyl, —N($C_{1-6}$alkyl)—$SO_2$—($C_{1-6}$alkyl), —$NR_aR'_b$, $C_{2-6}$alkoxycarbonyl or —PO($C_{1-4}$alkyl)$_2$; acyloxy; carboxy; $CONR_aR_b$; —PO($C_{1-4}$alkyl)$_2$; or $OCONR_cR_d$, wherein each of $R_c$ and $R_d$ independently is $C_{1-6}$alkyl.

Particularly preferred compounds of formula I are those wherein W is NH; $R_2$ is H; Z is —CH= or —$CCH_3$=; A is —CH= or —$CCH_3$=; $R_5$ is hydrogen, hydroxy, $C_{1-6}$alkoxy, $C_{1-6}$alkyl substituted by —$SO_2$—$C_{1-6}$alkyl, —$SO_2NR_aR_b$, —$CONR_aR_b$, —NH—$SO_2$—$C_{1-6}$alkyl, —N($C_{1-6}$alkyl)—$SO_2$—$C_{1-6}$alkyl or —PO($C_{1-4}$alkyl)$_2$, acyloxy, carboxy, $CONR_aR_b$, PO($C_{1-4}$alkyl)$_2$ or $OCONR_cR_d$.

Compounds of formula I wherein W is $NR_1$; $R_2$ is H; Z is —N=; A is —CH= or —$CCH_3$=; $R_5$ is hydroxy or $C_{1-6}$ alkoxy are also particularly preferred.

More particularly preferred compounds of formula I are those wherein W, $R_2$, Z, A and $R_5$ have one of the significances given above and B is a radical

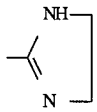

N or a radical of formula (b).

Compounds of formula I may exist in free, in salt form, in solvate or hydrate form. Salt forms may include acid addition salts and salt forms obtainable when $R_5$ is carboxy. Suitable pharmaceutically acceptable acid addition salt forms for use in accordance with the present invention as hereinafter described include, for example, the hydrochloride, sulfate, acetate, oxalate, maleinate and fumarate salts. When $R_5$ is carboxy, suitable salts are e.g. alkali metal salts such as sodium or potassium, or substituted or unsubstituted ammonium salts.

It will be appreciated that compounds of formula I, wherein X--Y is —$CR_8$=N— and B is a radical of formula (b')

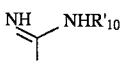 (b')

may exist as tautomers:

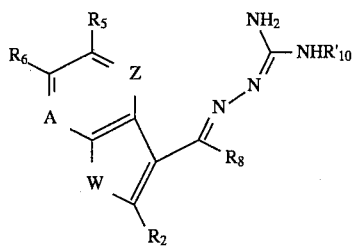

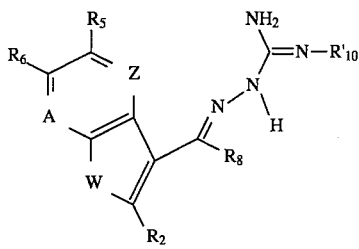

wherein $R_2$, $R_5$, $R_6$, $R_8$, A, W, Z and $R'_{10}$ are as defined above. Compounds of formula I wherein Z is —N=and $R_5$ is hydroxy may also exist as tautomers:

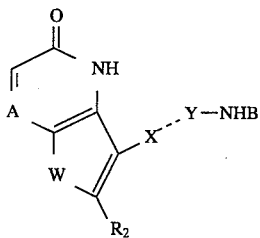

wherein W, A, $R_2$, B and X---Y are as defined above.

It is to be understood that where tautomeric forms occur, the present invention embraces all tautomeric forms and their mixtures, i.e. although compounds of formula I are defined for convenience by reference to one guanidino form only or to the 5-oxo form only, the invention is not to be understood as being in any way limited by the particular nomenclature or graphic representation employed. Similar considerations apply in relation to starting materials exhibiting guanidino-tautomerism or oxy/hydroxy tautomerism as hereinafter described.

In a further aspect the present invention also-provides a method for the production of compoundsof formula I, which method comprises:

a) for the production of a compound of formula I wherein X--Y is —$CR_8$=N— reacting a compound of formula II,

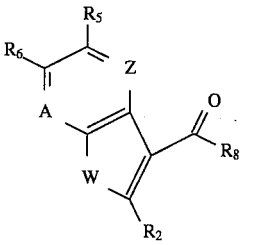 (II)

wherein A, W, Z, $R_2$, $R_5$, $R_6$ and $R_8$ are as defined above, with a compound of formula III, $H_2N$—NHB (III)

wherein B is as defined above; or b) for the production of a compound of formula I wherein X--Y is —CHR₈—NH—hydrogenating a compound of formula I wherein X--Y is —CR₈=N—; or c) for the production of a compound of formula $I_x$, wherein B is a radical of formula (b'), subjecting to alkylation, acylation or carbamoylation a compound of formula Ia,

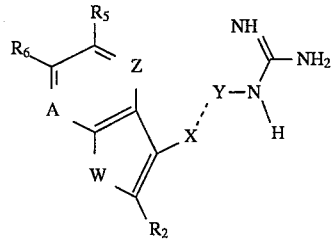
(Ia)

wherein A, W, Z, R₂, R₅, R₆ and X--Y are as defined above, d) for the production of a compound of formula I wherein R₅ is hydroxy subjecting to ether cleavage a compound of formula Ib

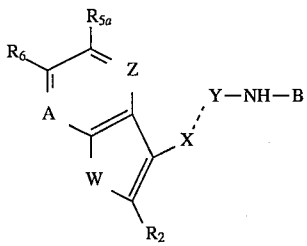
(Ib)

wherein

A, W, Z, R₂, R₆, X--Y and B are as defined above, and $R_{5a}$ is a cleavable ether group; or e) for the production of a physiologically-hydrolyzable and -acceptable ether or ester of a compound of formula I wherein R₅ is hydroxy etherifying or acylating a compound of formula I wherein R₅ is hydroxy and recovering compounds of formula I or a physiologically-hydrolyzable and -acceptable ether or ester thereof thus obtained, in free form or in salt, solvate or hydrate form.

Process step a) may be performed analogously to known methods, e.g. conveniently in the presence of an acid, for example an inorganic acid such as hydrochloric acid or hydrobromic acid, or an organic acid such as acetic acid, p-toluene sulfonic acid or pyridinium p-toluenesulfonic acid. The reaction may conveniently be effected in the presence of a protic solvent, for example methanol, ethanol or isopropanol. The reaction may advantageously be performed at a temperature between room temperature and reflux temperature.

Process step b) may be carried out in accordance with known hydrogenation methods. When R₅ is benzyloxy it may simultaneously be cleaved to a hydroxy group.

Process step c) may be carried out by methods known in the art. Alkylation or acylation of the compounds of formula Ia may be conveniently effected by reaction with an alkyl, cycloalkyl or aryl halide or acyl halide or anhydride, respectively, preferably in the presence of a base, for example triethylamine or a Hunig base. Carbamoylation may be conveniently carried out, by reaction with an isocyanate such as $R_{14}NCO$, preferably in the presence of a solvent, for example dimethylformamide.

Process step d) may be effected analogously to methods known in the art for ether cleavage. When $R_{5a}$ is benzyloxy, it may for example conveniently be performed by hydrogenation in the presence of a catalyst, e.g. Pd on charcoal. This reaction may be carried out in a solvent, for example an alcohol, at a temperature of from room temperature to 60° C.

$R_{5a}$ may be alkoxy, substituted alkoxy, alkenyloxy or benzyloxy.

Process step e) may e.g. be effected by reacting a compound of formula I wherein R₅ is hydroxy with an acyl halide, preferably acyl chloride. Compounds of formula I wherein R₅ is pyridyl-carbonyloxy may be prepared by reacting a compound of formula I wherein R₅ is hydroxy with a nicotine acid halide. The reaction may conveniently be performed in a solvent such as trifluoroacetic acid or trifluoromethane sulfonic acid.

Starting materials of formula II or III are either known or may be prepared analogously to methods known and practiced in the art.

For example compounds of formula II wherein W is —NR₁— may be prepared according to the following reaction scheme:

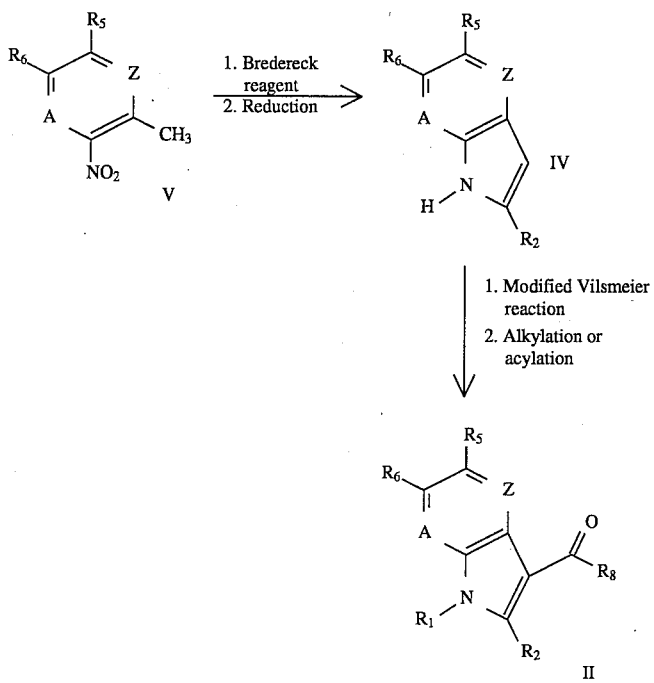

Compounds of formula IV above may be conveniently prepared by reacting a compound of formula V with a Bredereck reagent, for example $(CH_3)_2NCH(OCH_3)_2$, in the absence of a solvent or in the presence of a solvent such as pyrrolidine, followed by reduction, for example with hydrogen in the presence of a palladium catalyst or with hydrazine in the presence of Raney nickel.

Compounds of formula II wherein W is $—NR_1—$ may conveniently be produced by submitting a compound of formula IV to a modified Viismeier reaction and then alkylating or acylating.

The modified Viismeier reaction may be performed by using a dimethyl alkylamide in the presence of $POCl_3$ according to methods known in the art. Alkylation or acylation may be effected in a known manner, for example in the presence of a base, e.g. $K_2CO_3$ or $C_2H_5MgBr$, in a solvent such as dimethylformamide or tetrahydrofuran.

Compounds of formula III wherein B is a radical of formula (b) wherein $X_2$ is other than $—SR_{20}$ may conveniently be prepared by reacting a compound of formula VI

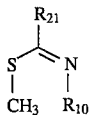

wherein $R_{10}$ is as defined above and $R_{21}$ is either $—NR_3R'_{10}$ or $—NHNH_2$ either with hydrazine when $R_{21}$ is $—NR_3R'_{10}$, or with an amine of formula $NHR_3R'_{10}$ when $R_{21}$ is $—NHNH_2$. The reaction may advantageously be carried out by heating at reflux temperature. It may be conveniently performed in a solvent, for example an alcohol such as methanol or ethanol, water or dimethylformamide, in the absence or in the presence of a basic compound, for example potassium hydroxide or carbonate.

Compounds of formula III wherein B is a radical of formula (b) wherein $X_2$ is $—SR_{20}$ may conveniently be prepared by alkylating a compound of formula VII

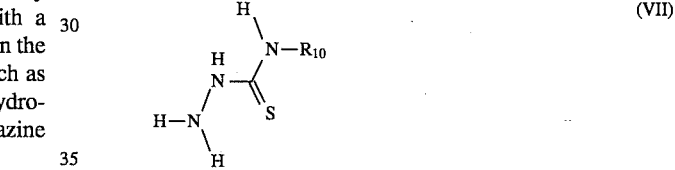

with a $R_{20}$-yielding compound, in accordance with known methods.

Insofar as the production of the starting materials is not particularly described, the compounds are known or may be prepared analogously to methods known and practiced in the art, or as disclosed in the following examples.

The following examples are illustrative of the invention. All temperatures are in °C.

The following abbreviations are used:

THF=tetrahydrofuran

DMF=dimethylformamide

EtOH=ethanol

MeOH=methanol

AcOEt=ethyl acetate (F)=foaming (S)=sintering

EXAMPLE 1

5-Hydroxy-indole-3-carboxaldehyde amino[3-(2'-pyrrolidinone-1-yl)-propylamino]methylenehydrazone To a solution of 0.9 g 5-hydroxy-indole-3-carboxaldehyde diaminomethylenehydrazone (4.1 mmol) in 10 ml THF containing 2 ml DMF and 0.9 ml Et$_3$N (6.2 mmol) are added at room temperature 1.3 g 3-(2'-pyrrolidinone-1'-yl)1-bromopropane (6.2 mmol). The mixture is stirred at 50° overnight. The mixture is then cooled to room temperature and the solvent is evaporated. The residue is chromatographed over SiO$_2$ (eluant: Toluene/EtOH/NH$_3$ 70:30:2.5) to yield the title compound as crystals. M.p.=158° (foaming).

Mass spectrum m/z (relative intensity): 343.3 (MH$^+$, 100); 217.2 (20); 168.2 (20); 143.2 (23).

EXAMPLE 2

5-Hydroxy-indole-3-carboxaldehyde amino(N-methyl-N-heptylamino)methylenehydrazone To a solution of 0.48 g 5-benzyloxy-indole-3-carboxaldehyde amino(N-methyl-N-heptylamino)methylene hydrazone (1.1 mmol) in EtOH there is added 0.25 g 10% Pd/C. The suspension is hydrogenated overnight at 45° C. Afterwards the suspension is filtered over silica gel, the solvent is evaporated and the residue is chromatographed over silica gel (eluant:toluene/EtOH/NH$_3$ 85:15:1) to yield the title compound. The pure material is crystallized from CH$_2$Cl$_2$/Hexane 2: 8.

M.p.=110° C. (sintering)

Mass spectrum m/z: 329 (M$^+$, 40); 128 (40); 111 (60); 73 (50).

The starting materials may be produced as follows:

a) To a solution of 3.2 g 5-benzyloxy-indole-3-carboxaldehyde (12.7 mmol) and 5.0 g 1-(N-methyl-N-heptyl)-3-N'-amino guanidine, hydroiodide (16.0 mmol) in 100 ml MeOH are added at 5° a solution of MeOH/HCl until pH=3. After 2 hours, the solvent is evaporated and the residue taken up in AcOEt. The solution is washed with a solution of Na$_2$CO$_{13}$ (2N). The organic layer is dried over sodium sulfate and the solvent is evaporated. The residue is chromatographed (eluant: Toluene/EtOH/NH$_3$ 85:15:0.5) to yield the title compound.

Mass spectrum m/z (relative intensity): 420 (MH$^+$, 100); 330 (7); 249 (4); 172 (16).

b) 1-(N-Methyl-N-heptyl)-3-N'-aminoguanidine, hydroiodide

A solution containing 4.7 g S-methyl isothiosemicarbazide hydroiodide (20 mmol) and 3.7 ml N-methyl N-heptylamine (22 mmol) in 30 ml methanol is refluxed for 6 hours. The solution is then cooled to room temperature and the solvent is evaporated to yield 1-(N-methyl-N-heptyl)-3-N'-amino-guanidine, hydroiodide. The resulting crude material is used for the next step without further purification.

EXAMPLE 3

5-Hydroxy-indole-3-carboxaldehyde amino(N-cyclohexylureido)methylenehydrazone

To a solution of 0.8 g 5-hydroxy-indole-3-carboxaldehyde diaminomethylenehydrazone (3.7 mmol) in 20 ml DMF is added over 5 min. at 0° a solution of 0.5 ml cyclohexyl isocyanate (4.0 mmol) in 5 ml DMF. The solution is stirred for 4 hours. The solvent is then evaporated and the residue chromatographied (eluant: Toluene/EtOH/NH$_3$ 85:15:0.5) to yield the title compound as crystals. M.p.=135° (foaming).

Mass spectrum m/z (relative intensity): 343 (MH$^+$, 100); 244 (50); 218 (85); 159 (33).

EXAMPLE 4

5-Hydroxy-6-fluoro-indole-3-carboxaldehyde amino(pentylamino)methylene hydrazone The title compound is prepared by following the procedure of Example 2. M.p.=125° (foaming).

5-Benzyloxy-6-fluoro-indole-3-carboxyaldehyde used as starting material may be produced as follows:

a) 2-Nitro-4-fluoro-5-benzyloxy-toluene

To a solution of 85.6 g 2-nitro-4-fluoro-5-hydroxy-toluene (0.5 mol) in 1300 ml acetone are added at room temperature 138 g K$_2$CO$_3$ (1.0 mol). 72 ml benzyl bromide (0.6 mol) are then added dropwise over 1 hour and the resulting mixture is stirred overnight at 60°. The solvent is evaporated and the residue taken up in AcOEt. The precipitate is removed by filtration and the solution is washed with water. The organic layer is dried over sodium sulfate, the solvent evaporated and the residue crystallized from hexane to yield 2-nitro-4-fluoro-5-benzyloxy-toluene. M.p.=95°.

Mass spectrum m/z: 261 (M$^+$).

b) 2-[1'-(N,N-Dimethylamino)-ethen-2'-yl]-4-benzyloxy-5-fluoronitrobenzene

A solution of 126 g 2-nitro-4-fluoro-5-benzyloxy-toluene (0.48 mol) in 200 g bis-dimethylamino-t-butoxy-methane (1.15 mol) is stirred overnight at 90°. Afterwards the solvent is evaporated and the residue crystallized from MeOH to yield the b) title compound as red crystals. M.p.=146°.

Mass spectrum m/z: 316 (M$^+$).

c) 5-Benzyloxy-6-fluoro-indole

A solution of 9.5 g b) compound (30.0 mmol) in 150 ml toluene and 30 ml THF containing 1 g Raney nickel is hydrogenated at room temperature. After 4 hours the suspension is filtered over hyflo and the solvent is evaporated. The residue is chromatographied under medium pressure (eluant: Toluene) to yield the b) title compound which is crystallized from hexane.

M.p.=126°.

Mass spectrum m/z: 241 (M$^+$).

d) 5-Benzyloxy-6-fluoro-indole-3-carboxaldehyde 3.3 ml POCl$_3$ (36.0 mmol) are added dropwise at 0° to 14 ml DMF (180.0 mmol). After 15 min. a solution of 7.30 g of the c) compound (30 mmol) in 14 ml DMF is added dropwise over 10 min. The mixture is stirred for 1 hour at room temperature, then diluted with cold water and a solution of 7.2 g NaOH in 50 ml water is then added dropwise. The precipitate is filtered and washed with water. The resulting solid is chromatographied over SiO$_2$ (eluant: CH$_2$Cl$_2$) and crystallized from ether to yield the d) title compound. M.p.=190°.

Mass spectrum m/z (relative intensity): 269 (M$^+$, 72); 178 (20); 150 (15); 91 (100); 65 (38).

EXAMPLE 5

5-Hydroxy-indole-3-carboxaldehyde amino(butyrylamido)methylenehydrazone

To a solution of 0.5 g 5-hydroxy-indole-3-carboxaldehyde diaminomethylenehydrazone (2.3 mmol) in 5 ml DMF are added dropwise a solution of 0.4 ml butanoic anhydride (2.5 mmol) in 5 ml DMF. After 7 hours at room temperature the solvent is evaporated and the residue is chromatographed over SiO$_2$ (eluant: Toluene/EtOH/NH$_3$85:15:0.3). The title compound is thus obtained and precipitated from hexane. M.p.=90° (foaming).

Mass spectrum m/z (relative intensity): 287 (M$^+$, 16); 217 (8); 200 (4); 158 (30); 98 (100); 70 (46).

EXAMPLE 6

5-Benzyloxy-indole-3-carboxaldehyde amino-(pentylamino)methylenehydrazone trifluoroacetate M.p.=138°.

EXAMPLE 7

5-Hexanoyloxy-indole-3-carboxaldehyde amino(pentylamino)methylenehydrazone trifluoroacetate To a solution of 1.0 g 5-hydroxy-indole-3-carboxaldehydeamino(pentylamino)methylenehydrazone (3.5 mmol) in 10 ml $CF_3CO_2H$ there is added 0.72 ml hexanoylchloride (5.2 mmol) at 0° C. After 3 hours the reaction is quenched with 2N $Na_2CO_3$ and the mixture is stirred for 20 min. AcOEt is added and the organic layer is separated, washed with brine and dried over $Na_2SO_4$. The solvent is evaporated and the residue is washed with ether to yield the crystalline title compound.

M.p.=205°.

Mass spectrum m/z: 385 ($M^+$, 20); 160 (30); 158 (25); 69 (100).

By following a procedure as disclosed above, the compounds of formula IA

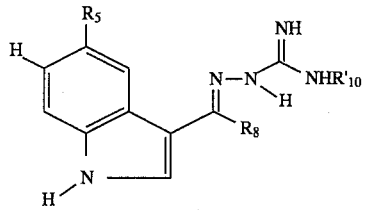

IA wherein $R_5$, $R_8$ and $R'_{10}$ are as defined in Table I thereafter, may be prepared.

TABLE I

| Ex. | $R_5$ | $R_8$ | $R'_{10}$ | M.P. |
|---|---|---|---|---|
| 8 | $OCH_2OCH_3$ | H | pentyl | 108° |
| 9 | $OCH_2CH=C(CH_3)_2$ | H | pentyl | amorph |
| 10 | OH | H | $-(CH_2)_3-NH-CO-C_6H_5$ | 179° (F.) |
| 11 | $OCO-N(CH_3)_2$ | H | pentyl | 90° (F.) |
| 12 | H | H | pentyl | 125° |
| 13 | $OCH_3$ | H | pentyl | 124°* |
| 14 | OH | H | pentyl | 128° (F.)** |
| 15 | OH | H | H | 247° hydrochloride |
| 16 | OH | $CH_3$ | H | 180° (F.) |
| 17 | OH | H | $-(CH_2)_2-N$ (2-oxopyrrolidinyl) | 165° |
| 18 | OH | H | $CH_3$ | 140° (F.) |
| 19 | OH | $CH_3$ | pentyl | 200° |
| 20 | $OC_2H_5$ | H | pentyl | 114° |
| 21 | $O-i-C_3H_7$ | H | pentyl | 90° |
| 22 | OH | H | 3,8-dimethyl-nonyl | 150° |
| 23 | OH | H | 3-(p-F-phenoxy)-propyl | 85° (F.) |
| 24 | OH | H | $-(CH_2)_2-NH-CO-C_6H_5$ | 110° (F.) |
| 25 | benzoyloxy | H | pentyl | 155° (F.) |
| 26 | $-O-CO-tert.C_4H_9$ | H | pentyl | amorph |
| 27 | OH | H | $-(CH_2)_3-N$(COC(CH_3)_2NH-CO-) | 130° (F.) |
| 28 | $OCH_3$ | H | $-(CH_2)_3-NH-CO-C_6H_5$ | amorph |
| 29 | $OCH_2OCH_3$ | H | $-(CH_2)_3-NH-CO-C_6H_5$ | amorph |
| 30 | $OCH_2CH=C(CH_3)_2$ | H | $-(CH_2)_3-NH-CO-C_6H_5$ | amorph |
| 31 | OH | H | $-S-(CH_2)_4-CH_3$ | 190° hydroiodide |
| 32 | COOH | H | pentyl | 310° hydrochloride |
| 33 | 3-pyridyl-carbonyloxy | H | pentyl | 95° |
| 34 | OH | H | 3-benzamido-propyl | 179° (F.) |
| 35 | $O-CO-N(C_2H_5)_2$ | H | pentyl | 75° (F.) |
| 36 | OH | H | $-(CH_2)_3-OH$ | 140° (F.) |
| 37 | $O-CH_2-CO-N(CH_3)_2$ | H | pentyl | 160° |
| 38 | OH | H | 3-benzimidazol-2-yl-propyl | amorph |
| 39 | OH | H | $-(CH_2)_3-NH-SO_2-C_6H_5$ | amorph |
| 40 | $O-CH_2-CH_2-N(CH_3)_2$ | H | pentyl | amorph |
| 41 | $O-(CH_2)_2-O-CH_3$ | H | pentyl | amorph |
| 42 | $O-(CH_2)_2-OH$ | H | pentyl | amorph |

TABLE I-continued

| Ex. | $R_5$ | $R_8$ | $R'_{10}$ | M.P. |
|---|---|---|---|---|
| 43 | OH | H | octyl | amorph |
| 44 | $Si(CH_3)_3$ | H | pentyl | amorph |
| 45 | isobutoxy | H | pentyl | amorph |
| 46 | $OCH_2CS-N(CH_3)_2$ | H | pentyl | amorph |
| 47 | OH | H | phenethyl | 130° (F.) |
| 48 | OH | H | $-(CH_2)_3-N(CH_3)$-benzoyl | 202° |
| 49 | 2,3-di(OH)-propoxy | H | pentyl | 105° (S.) |
| 50 | $NH_2$ | H | pentyl | 100° (F.) |
| 51 | acetoxy | H | pentyl | 225° hydro-iodide |
| 52 | $PO(CH_3)_2$ | H | pentyl | 90° (F.) |
| 53 | $COOCH_3$ | H | pentyl | 184° |
| 54 | CN | H | pentyl | 138° (F.) |
| 55 | $NO_2$ | H | pentyl | 153° |
| 56 | $CH_2-SO_2-NHCH_3$ | H | pentyl | 98° (S.) |
| 57 | $OCH_2OCO$-t.butyl | H | pentyl | amorph |
| 58 | $CH_2-SO_2-NHCH_3$ | H | $CO-NHC_6H_{11}$ | 180° (F.) |
| 59 | OH | H | 3-phenyl-propyl | amorph |
| 60 | OH | H | o-chlorophenethyl | 122° (F.) |
| 61 | $OCH_3$ | H | phenethyl | 202° |
| 62 | $CH_2-CH_2-SO_2-CH_3$ | H | pentyl | amorph |
| 63 | $CONH_2$ | H | pentyl | 130° (F.) |
| 64 | $CON(CH_3)_2$ | H | pentyl | 100° (F.) |
| 65 | OH | H | 4-chlorophenethyl | 115° (F.) |
| 66 | OH | H | 3-MeO-phenethyl | 120° (F.) |
| 67 | F | H | phenethyl | 212° (F.) |
| 68 | $CH_2-N(CH_3)_2$ | H | pentyl | amorph |
| 69 | $CONH_2$ | $CH_3$ | pentyl | 246° (1) |
| 70 | OH | H | 3,4-di-Cl-phenethyl | 274° (1) |
| 71 | F | H | 3-MeO-phenethyl | 185° (1) |
| 72 | H | H | $CH_2CH_2CONH_2$ | amorph (1) |
| 73 | $CH_2-CH_2-NH-SO_2CH_3$ | H | pentyl | 105° (1; F.) |
| 74 | $CH_2-NH-SO_2CH_3$ | H | pentyl | 204° (1; F.) |
| 75 | $SO_2-NH_2$ | H | pentyl | 120° (F.) |
| 76 | $CH(CH_3)-OCH_3$ | H | pentyl | 115° (1; F) |
| 77 | $OCH_3$ | H | 3,4-di-Cl-phenethyl | 209° (1) |

*m.p. hydrogenomaleate = 190° C.
**m.p. hydrochloride = 228° C.
(1): hydrochloride By following a procedure as disclosed above, the compounds of formula IB

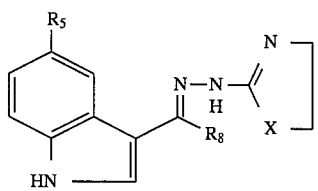

IB wherein $R_5$, $R_8$ and X are as defined in Table II below, may be prepared.

TABLE II

| Ex. | $R_5$ | $R_8$ | X | M.P. |
|---|---|---|---|---|
| 78 | OH | H | NH | 178° (F) |
| 79 | OH | $CH_3$ | NH | 240° |
| 80 | OH | H | $CH_2$ | 297° chlorhydrate |
| 81 | OH | H | S | 165° |
| 82 | $OCH_3$ | H | $CH_2$ | 248° chlorhydrate (F) |
| 83 | $CON(CH_3)_2$ | H | NH | 225° |
| 84 | $CH_2SO_2NHCH_3$ | H | NH | 253° |
| 85 | $CH_2SO_2NHCH_3$ | $CH_3$ | NH | 249° |
| 86 | OH | H | NH | 140° (F) |

EXAMPLE 87

5-Hydroxy-3-[(N'-2'-imidazolin-4'-onyl)-hydrazomethyl]-indole

M.p.=110° (F).

EXAMPLE 88

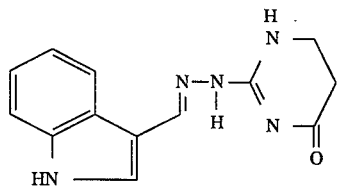

M.P.=239°

By following a procedure as disclosed above, the compounds of formula IC

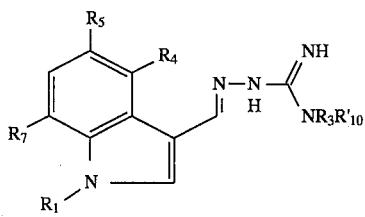

(IC)

wherein $R_1$, $R_3$, $R_4$, $R_5$, $R_7$ and $R'_{10}$ are as defined in Table III below, may be prepared.

TABLE III

| Ex. | $R_1$ | $R_4$ | $R_7$ | $R_5$ | $R_3$ | $R'_{10}$ | M.P. |
|-----|-------|-------|-------|-------|-------|-----------|------|
| 89  | H     | H     | CH$_3$ | OH   | H     | pentyl    | 130° (F) |
| 90  | C$_2$H$_5$ | H | H | OH | H | pentyl | 144° |
| 91  | H     | CH$_3$ | H    | OH   | H     | pentyl    | 105° (F) |
| 92  | H     | OH    | H     | H     | H     | pentyl    | 147° |
| 93  | H     | H     | H     | OH    |       | piperidino |       164° (F) |
| 94  | H     | H     | H     | OH    |       | perhydroindolyl | 170° (S) |
| 95  | H     | H     | H     | OH    | CH$_3$ | pentyl   | 100° (F) |
| 96  | H     | H     | H     | OCH$_3$ | CH$_3$ | pentyl | 139° |
| 97  | H     | H     | CH$_3$ | OH   | CH$_3$ | pentyl   | 120° (S) |
| 98  | H     | H     | CH$_3$ | OCH$_3$ | CH$_3$ | pentyl | amorph |
| 99  | C$_2$H$_5$ | H | H | OH | CH$_3$ | pentyl | 138° (F) |
| 100 | H     | CH$_3$ | H    | OH   | H     | 3-benzimidazol-2-yl-propyl | amorph |
| 101 | H     | H     | CH$_3$ | H   | H     | 3-benzimidazol-2-yl-propyl | 120° (F) |
| 102 | H     | H     | OCH$_3$ | H  | H     | 3-benzimidazol-2-yl-propyl | 135° (F) |
| 103 | H     | H     | CH$_3$ | OCH$_3$ | H  | 3,4-di-Cl-phenethyl | 220° (1) |

By following a procedure as disclosed above the compounds of formula ID

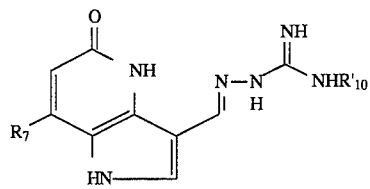

(ID)

wherein $R_5$ and $R'_{10}$ are as defined in Table IV below, may be prepared.

TABLE IV

| Ex. | $R_5$ | $R'_{10}$ | M.P. |
|-----|-------|-----------|------|
| 104 | OCH$_3$ | pentyl | 107° |
| 105 | OH    | pentyl    | 155° |
| 106 | OH    | 3-benzimidazol-2-yl-propyl | 150° (S) |
| 107 | OCH$_3$ | 3-benzimidazol-2-yl-propyl | 98° (F) |

By following a procedure as disclosed above, the compounds of formula IE (IE)

wherein $R_7$ and $R'_{10}$ are as defined in Table V below, may be prepared.

TABLE V

| Ex. | $R_7$ | $R'_{10}$ | M.P. |
|-----|-------|-----------|------|
| 108 | H     | pentyl    | amorph |
| 109 | H     | phenethyl | 192° |
| 110 | CH$_3$ | pentyl   | 195° |
| 111 | H     | CH$_2$CH$_2$NHCOC$_6$H$_5$ | 220° |
| 112 | H     | benzyl    | 203° |

EXAMPLE 113

(7-Azaindole)-3-carboxaldehyde amino (pentylamino)methylenehydrazine.

M.p.=78° ( Sintering).

EXAMPLE 114

5-Hydroxy-6-fluoro-indole-3-carboxaldehyde amidino-hydrazone

M.p.=168° (F).

5-(Dimethylphosphine oxide)-indole-3-carboxaldehyde, used as starting material for the production of the compound of Example 52 may be prepared according to Example 4 d) from indol-5-dimethylphosphine oxide.

Indole-5-dimethylphosphine oxide may be prepared as follows:

EXAMPLE 115

Indole-5-dimethylphosphine oxide a) N-benzyl-indoline-5-(dimethylphosphine oxide)

A solution of t-BuLi in hexane (10 mmol, 1.7M) is added at −78° to a solution of 5-bromo-N-benzyl-indoline (5 mmol) in 30 ml ether. After 10 minutes a solution of ClPO(Me)2 (10 mmol) in 10 ml THF is added thereto. The reaction is allowed to warm up to room temperature over 6 hours. Water and AcOEt are added, the organic layer is separated and the aqueous phase is extracted with AcOEt. The combined organic phases are washed with brine, dried and the solvent is evaporated. The residue is chromatographed over SiO2 (eluant: CH$_2$Cl$_2$/MeOH 95:5) to yield the a) title compound. M.p.=180°.

b) indoline-5-(dimethylphosphine oxide)

A solution of compound a) (1.5 mmol) in 20 ml MeOH containing 0.2 g Pd/C is hydrogenated over two hours. The solution is filtered over Hyflo and the solvent is evaporated to yield the b) title compound.

c) indole-5-(dimethylphosphine oxide)

A solution of compound b) (1.5 mmol) in 25 ml xylene containing 100 mg Pd/C is refluxed for 3 hours. The solution is filtered over Hyflo and the catalyst washed with $CH_2Cl_2$. The solvent is evaporated to yield the c) title compound. M.p.=195°.

5-Hydroxy-benzothiophene-3-carboxyaldehyde and 5-methoxy-benzothiophene-3-carboxyaldehyde used as starting materials for the preparation of the compounds of Examples 104 to 107 may be prepared as follows:

EXAMPLE 116

5-Methoxy-benzothiophene-3-carboxyaldehyde a) (4-methoxy-benzyl) acetonyl sulfide 0.165 Mol sodium hydride is added portionwise at 0° to a solution of 4-methoxy-thiophenol (0.15 mol) in 300 ml THF. After 1 hour chloracetone (0.165 mol) is added. The mixture is stirred overnight at room temperature. Thereafter the solvent is evaporated and the mixture is dissolved in $CH_2Cl_2$ and washed with 2 N $Na_2CO_3$. The organic phase is dried and the solvent is evaporated to yield the title a) compound which is used without further purification.

b) 3-methyl-5-methoxy-benzothiophene 0.15 Mol of compound a) is added over 1 hour at reflux to a solution of polyphosphoric acid (0.17 mol) in 1 liter chlorobenzene. The solution is stirred at reflux overnight. The mixture is filtered and the filtrate is evaporated. The crude product is chromatographied over $SiO2$ (eluant: hexane) to yield the title b) compound.

c) 5-methoxy-3-bromomethyl-benzothiophene 0.01Mol NBS and a crystal of dibenzoylperoxide are added to a solution of compound b) (0.01 mol) in 60 ml tetrachlorocarbone. The mixture is stirred at reflux for 1.5 hours. The suspension is filtered and the filtrate is evaporated. The resulting oil crystallizes on cooling and is used without further purification.

d) 5-methoxy-benzothiophene-3-carboxaldehyde 0.09 Mol hexamethylene tetraamine is added to a solution of compound c) (0.08 mol) in 150 ml chloroform. The mixture is stirred at reflux for 6 hours. Ether is added to the suspension after cooling and the solid is isolated by filtration. The residue is dissolved in 100 ml 50% $CH_3COOH$ and the mixture is refluxed for 3 hours. 130 ml water and 25 ml concentrated $HC_1$ are then added and the mixture is refluxed for 5 further minutes. The mixture is cooled with ice. The title d) compound crystallizes is isolated by filtration and washed with water. M.p.=50°.

EXAMPLE 117

5-hydroxy benzothiophene-3-carboxaldehyde

A solution of BBr3 (0.07 mol) in 15 ml $CH_2Cl_2$ is added at 0° to a solution of 0.014 mol 5-methoxy-benzothiophene-3-carboxaldehyde in 80 ml $CH_2Cl_2$. After 4 hours 2 N $Na_2CO_3$ is added until pH=7. The organic solvent is evaporated and the suspension is filtered. The solid is washed with water to yield crude title compound which is recrystallized from $CH_3OH/H_2O$. M.p.=200°.

The compounds of formula I and their pharmaceutically acceptable salts (hereina#ter referred to as compounds of the invention) exhibit pharmaceutical activity and are, therefore, useful as pharmaceuticals.

In particular, compounds of the invention have a stimulatory effect on gastrointestinal motility as may be shown in standard test models, for example as follows:

Monopolar electrodes are implanted on the serosal side of the gut wall along the small intestine of Beagle dogs. From these electrodes, signals are fed into a preamplifier and filtered for the registration of low and high frequency potentials, in order to separate slow waves from spikes. The number of spike bursts occuring in 2 min. periods are determined. From this the following data are extracted: duration of phase I—III, interval between 2 consecutive phase III blocks, and propagation velocity. One or two cycles are recorded prior to drug administration which is done subcutaneously 10–15 min after a Phase III has passed the most distal electrodes. Control experiments are performed routinely by means of solvent administration. In fed dogs, the number of spikes per 30 min. is determined additionally. In this test the compounds of the invention stimulate myoelectric activity at dosages of the order of from about 0.001 to 10 mg/kg s.c.

In this test it has for example been determined that for the compound of Example 13 the threshold dose for stimulating myoelectric activity is 0.03 mg/kg s.c. compared with Cisapride for which the threshold dose is 0.3 mg/kg s.c. in the same test.

Furthermore, the stimulatory effect on gastrointestinal motility of compounds of the invention is also indicated e.g. by their effects on the peristaltic reflex in the isolated guinea-pig ileum.

Male guinea-pigs, 200–400 g are stunned and bled. Segments of terminal ileum, 4–5 cm long, are removed and suspended as described by Trendelenburg in Arch. Exp. Path. Pharmakol., 81, 55–129 (1917), in a 20 ml organ bath under an initial load of 1 g. The tissue is bathed with a modified Krebs solution (NaCl 118.6; $CaCl_2$ 2.7; KCl 4.7; $KH_2PO_4$ 1.2; $MgSO_4$ 0.1; $NaHCO_3$ 25.0; and glucose 5.6 mM), maintained at 37° C. and bubbled with 5% $CO_2$ in oxygen. Peristalsis is elicited for 30 s by increasing the intraluminal pressure from zero by 1 to 4 cm $H_2O$. Measurements are made of longitudinal muscle responses by using an isotonic force-displacement transducer and of circular muscle activity by employing a pressure transducer. The area under the curve (AUG) of peristaltic contractions is determined and concentration response curves are established by plotting the AUC representing the circular and longitudinal muscle activity. Each preparation is used as its own control, taking the peristaltic activity before the administration of the compounds to be tested as 100%. Compounds to be tested are added to the serosal side and are left in contact with the tissue for 15 min. In this test compounds of the invention have a stimulatory effect on the peristaltic activity at concentrations of the order of from about $10^{-10}$M to $10^{-7}$M.

In this test it has for example been determined that the compound of Example 13 has a stimulatory effect on the peristaltic activity with a half-maximal effect obtained at a concentration of $10^{-8}$ M ($pEC_{50}$ value of 9.0) compared with cisapride or metoclopramide which have a $pEG_{50}$ value of <7 and 5.7, respectively.

Compounds of the invention are therefore useful for the treatment of gastrointestinal motility disorders, for example to normalize or to improve the gastric emptying and intestinal transit in subjects having a disturbed motility, e.g. gastro-oesophageal reflux disease, decreased peristalsis of the oesophagus and/or stomach and/or small and/or large intestine, or to treat oesophagitis, gastroparesis, dyspepsia, non-ulcer dyspepsia, pseudo-obstruction, impaired colonic transit, ileus, irritable bowel syndrome, constipation, epigastric pain, postoperative gut atony, recurrent nausea and vomiting, anorexia nervosa or dyskinesias of the biliary system.

Furthermore the compounds of the invention are also indicated for use in the treatment of dyskinesias of the urinary bladder, the modulation of cortisol/aldosterone release, or for improving memory and learning.

For the above uses the required dosage will of course vary depending on the mode of administration, the particular condition to be treated and the effect desired. In general however, satisfactory results are achieved at dosage rates of from about 0.01 to about 10 mg/kg animal body weight, e.g. from about 0.01 to about 1 mg/kg, for parenteral use, and at dosage rates of from about 0.1 to about 10 mg/kg for oral use. Suitable daily dosage rates for larger mammals, for example humans, are thus of the order of from about 0.01 to about 3 mg/day, e.g. from about 0.01 to about 1 mg/day for parenteral use, and of the order of from about 0.1 to about 3 mg/day for oral use, conveniently administered once, in divided dosages 2 to 4 ×/day, or in sustained release form. Unit dosage forms for oral administration accordingly comprise from about 0.0025 to about 1.5 mg active ingredient (i.e. compound or pharmaceutically acceptable salt of the invention) admixed with an appropriate solid or liquid, pharmaceutically acceptable, diluent or carrier therefor.

In accordance with the foregoing the present invention also provides:

i) A method for treating gastrointestinal motility disorders, e.g. by stimulating the motility of the gastrointestinal system, dyskinesias of the urinary bladder, modulating cortisol/aldosterone release or improving memory and learning in a subject in need thereof, which method comprises administering to said subject an effective amount of a compound of the invention or a pharmaceutically acceptable salt thereof.

It has further been found that compounds of the invention have an antiserotoninergic effect specifically at the 5-HT$_4$ receptors as may be shown in standard test models, for example as follows:

The isolated longitudinal muscle of the guinea pig ileum with its adhering myenteric plexus is a well established model which permits investigations of the mechanism of action of various neurotransmitters.

Method

Male guinea pigs (200–400 g) are killed by a blow on the head and exsanguinated. A length of small intestine is removed about 2 cm from the ileo-caecal valve. The ileum is stretched over a glass rod and the mesentery is carefully removed. By strocking tangentially away from the mesenteric attachment with a wad of cotton wool, the longitudinal muscle layer is separated and stripped from the underlying circular muscle. Longitudinal muscle strips, 3–4cm length, are mounted in a 10 ml organ bath containing Tyrode solution at 37° C. and bubbled with a 5% carbon dioxide in oxygen. The Tyrode solution is of the following composition (mmol/1): NaCl 137.0; CaCl$_2$ 1.8; KCl 2.7; MgCl$_2$ 1.05; NaHCO$_3$ 11.9; NaHPO$_4$ 0.4; glucose 5.6; and methysergide 0.1 μM. The strips are maintained under a resting tension of 500 mg. Contractions are recorded with an isotonic pendulum lever. After equilibration for 30 min a set concentration of carbachol is applied in 10 min intervals until a consistent reaction is achieved.

Production of the concentration/reaction curve

Non-cumulative concentration-response curves for 5-HT are established by adding increasing concentrations of the agonist to the organ bath at intervals of at least 15 min. Preceding experiments showed that the intervals were long enough to avoid tachyphylaxis. Each concentration is left in contact with the tissue for 1 min. Each strip is only used to record two concentration-response curves; the first for 5-HT alone and the second for 5-HT in the presence of a set concentration of antagonist, each strip thus serving as its own control. Antagonists are allowed to preequilibrate for at least 10 min prior to addition of 5-HT. The contractions expressed as percentage of the maximal response to 5-HT obtained from several preparations are plotted as mean values in order to obtain log-concentration-response curves. Inhibition constants are expressed in the form of pA$_2$ values which are graphically determined according to conventional methods (Arunlakshana et al, 1959, McKay 1978).

In this test 5-HT elicits a concentration-dependent contractile effect. 5-HT induces its major contractile effects in the longitudinal muscle strip of the guinea pig ileum by releasing substance P from nerve endings within this tissue. Its effect is mediated by two different 5-HT receptors. At low concentrations 5-HT activates a neuronal receptor which causes substance P release. The liberated substance P activates neuronal substance P receptors and this causes the release of acetylcholine which subsequently activates muscarinic receptors located on smooth muscle cells and brings about contraction. At higher concentrations 5-HT activates a second neuronal receptor which results in release of substance P to cause activation of substance P receptors on smooth muscle cells and thereby exerting contraction.

Compounds of the invention block preferentially the high affinity 5-HT$_4$ receptors thereby inhibiting 5-HT-induced contraction e.g. at concentrations from about $10^{-8}$ to about $10^{-6}$ mol/1. They exert less antagonistic activity at the low affinity 5-HT$_3$ receptor sites.

In this test it has for example been determined that the compounds of Examples 89, 90 and 97 have a pA$_2$ value of 8.1, 8.0 and 8.3 respectively.

Compounds of the invention are therefore useful for the treatment of gastro-intestinal motility disorders such as tachygastria, problems of gastric emptying due to tachygastria, irritable bowel syndrome, intestinal spasms, intestinal cramps, constipation due to increased large intestinal tone, gastro-esophageal reflux disease and dyskinesias of the biliary system.

Compounds of the invention also inhibit gastric lesions induced by necrotizing agents as indicated in standard tests, e.g. using rats with ethanol-induced gastric lesions.

The tests are carried out employing male rats (200–250 g) fasted overnight but with free access to water. The test substance is administered s.c. or orally by a metal stomach tube. Absolute ethanol is given orally 30 min after administration of the test substance and the animals are killed 1 hour later. The stomach is cut open along the greater curvature and pinned flat. Hemorrhagic erosions are quantified in two ways: area and length of the erosions.

On s.c. administration of a compound of the invention as test compound at a dosage of from ca. 0.1 μg/kg to 10 mg/kg, substantial inhibition of the gastric lesions induced by ethanol is observed compared with results for control groups receiving placebo in lieu of the test substance.

Compounds of the invention are accordingly indicated for use in the prophylactic or curative treatment of gastrointestinal disorders such as peptic ulcer diseases.

The compounds of the invention are further indicated for treating diarrhea, inflammatory diseases of the stomach and bowel, e.g. gastritis, duodenitis, including inflammatory bowel disease, nausea and vomiting. Furthermore they are also indicated for the treatment of arrhythmias, tachycardia, dyskinesia of the urinary bladder, e.g. incontinence, for reducing the occurrence of stroke, or for modulating stress responses.

For the above uses the required dosage will of course vary depending on the mode of administration, the particular condition to be treated and the effect desired. In general however, satisfactory results are achieved at dosage rates of from about 0.1 µg/kg to about 1 mg/kg animal body weight, e.g. from about 0.1 µg/kg to about 0.1 mg/kg, for parenteral use, and at dosage rates of from about 1 µg/kg to about 1 mg/kg for oral use. Suitable daily dosage rates for larger mammals, for example humans, are thus of the order of from about 5 µg to about 5 mg/day for parenteral use, and of the order of from about 0.1 to about 100 mg/day for oral use, conveniently administered once, in divided dosages 2 to 4 ×/day, or in sustained release or retard form. Unit dosage forms for oral administration accordingly comprise from about 0.025 to about 50 mg of a compound of the invention admixed with an appropriate solid or liquid, pharmaceutically acceptable, diluent or carrier therefor.

In accordance with the foregoing the present invention also provides:

ii) A method for the treatment of any of the above mentioned disorders or conditions in a subject in need thereof, which method comprises administering to said subject an effective amount of a compound of the invention or a pharmaceutically acceptable salt thereof;

Furthermore it has been found that the compounds of the invention have an antagonist effect at the central 5HT-1C receptors.

Compounds of the invention have a potent binding affinity to central 5HT-1C receptors as e.g. measured according to the method disclosed by D. Hoyer et al., Eur. J. Pharmacol., 118, 13–23 (1985).

Compounds of the invention antagonize the hypolocomotion induced in rats by administration of m-chlorophenylpiperazine (mCPP) according to the method disclosed by G. A. Kennett and G. Curzon, Br. J. Pharmacol., 94, 137–147 (1988). In this test compounds of the invention counteract the mCPP induced locomotion after administration at dosages of from about 0.1 to 30 mg/kg p.o.

Compounds of the invention are therefore useful for the prophylactic treatment of migraine or for the treatment of psychiatric disorders e.g. anxiety, obsessive compulsive disorders, panic attacks, depression, bulimia, schizophrenia, situations of increased intracranial pressure and priapism.

For the above uses the required dosage will of course vary depending on the mode of administration, the particular condition to be treated and the effect desired. In general however, satisfactory results are achieved at dosage rates of from about 0.1 to about 100 mg/kg animal body weight. Suitable daily dosage rates for larger mammals, for example humans, are thus of the order of from about 0.5 to about 300 mg/day, conveniently administered once, in divided dosages 2 to 4 ×/day, or in sustained release form.

In accordance with the foregoing the present invention also provides:

iii) A method of prophylactic treatment of migraine or for treating psychiatric disorders in a subject in need thereof, which method comprises administering to said subject an effective amount of a compound of the invention or a pharmaceutically acceptable salt thereof.

Compounds of the invention also have an agonist effect on 5HT-1D receptors. Their binding affinity to 5HT-1D receptors has been determined e.g. according to the method disclosed by C. Waeber et al., Naunyn-Schmiedeberg,s Arch. Pharmacol., 337, 595–601 (1988). Compound of Example 63 has a pKD value of 8.55.

The agonist effect is further demonstrated in the following assay:

Anterior cerebral arteries are excised from pig brains obtained from the local slaughterhouse. Circular segments of 3–4 mm length are mounted between two L-shaped metal prongs and placed in temperature-controlled (37° C.) organ baths filled with Krebs solution that is continuously gassed with 5% $CO_2$ in oxygen. Agonist-induced vascular contractions are measured isometrically. In order to measure only 5-HT1D receptor mediated effects, ketanserin ($10^{-7}$M), which prevents contractions via 5-HT2 receptors, is added to the bath solution. Compounds of the invention induce vascular contractions at a concentration of from $10^{-10}$ to $10^{-5}$M, particularly $10^{-9}$ to $10^{-7}$M. In this test, it has been determined that compound of Example 63 has a pD2 value of 9.0.

Compounds of the invention are therefore useful in treating conditions associated with cephalic pain, in particular in the treatment of migraine, cluster headache, chronic paroxysmal hemicrania and headache associated with vascular disorders and in alleviating the symptoms associated therewith.

For the above uses the required dosage will of course vary depending on the mode of administration, the particular condition to be treated and the effect desired. In general however, satisfactory results are achieved at dosage rates of from about 0.1 to about 100 mg/kg animal body weight. Suitable daily dosage rates for larger mammals, for example humans, are thus of the order of from about 0.5 to about 300 mg/day, conveniently administered once, in divided dosages 2 to 4×/day, or in sustained release form.

In accordance with the foregoing the present invention also provides:

iv) A method for treating conditions associated with cephalic pain, e.g. as indicated above in a subject in need thereof, which method comprises administering to said subject an effective amount of a compound of the invention or a pharmaceutically acceptable salt thereof.

The compounds of the invention may be administered by any conventional route, in particular nasally, enterally, preferably orally, e.g. in the form of tablets or capsules, or parenterally e.g. in the form of injectable solutions or suspensions or in a suppository form.

The compounds of the invention may be administered in free form or in pharmaceutically acceptable salt form. Such salts may be prepared in conventional manner and exhibit the same order of activity as the free compounds. Suitable pharmaceutically acceptable salts of the compounds of the invention include for example the hydrochlorides.

Furthermore the present invention also provides:

v) A compound of the invention or a pharmaceutically acceptable salt thereof, for use as a pharmaceutical, e.g. in any of the methods as indicated above;

vi) A pharmaceutical composition comprising a compound of the invention as hereinbefore defined, or a pharmaceutically acceptable salt thereof, together with a pharmaceutically acceptable diluent or carrier therefor. Such compositions may be manufactured in conventional manner, e.g. by mixing of the ingredients.

Compounds of formula I wherein $R_1$ is hydrogen, A is —N= or —CH= and Z is —CH=, or wherein $R_1$ is H, A is —CH=, Z is —N= or —CH= and $R_5$ is hydroxy or $C_{1-6}$alkoxy have e.g. a stimulatory effect on gastrointestinal motility and are therefore useful in the method of the invention for treating motility disorders, e.g. by stimulating the motility of the gastrointestinal system as indicated above, for treating dyskinesias of the urinary bladder, modulating cortisol/aldosterone release or improving memory and learning. Compounds of Examples 13 and 108 are preferred.

Compounds of formula I wherein $R_1$ in W and/or $R_7$ in A is other than hydrogen have e.g. an antiserotoninergic effect specifically at the 5-$HT_4$ receptors and inhibit gastric lesions induced by necrotizing agents and are therefore useful as an antiulcer or antimotility agent in the method of the invention for treating gastrointestinal disturbances and for the prophylactic or curative treatment of peptic ulcer diseases. They are also indicated for treating diarrhea, inflammatory diseases of the stomach and bowel, e.g. gastritis, duodenitis, including inflammatory bowel disease, nausea and vomiting, arrhythmias, tachycardia, dyskinesia of the urinary bladder, e.g. incontinence, for reducing the occurrence of stroke, or for modulating stress responses. Compounds of Examples 89, 90 and 97 are preferred.

Compounds of formula I wherein $R_5$ is hydrogen, hydroxy, $C_{1-6}$alkoxy or nitro, $R_2$ is hydrogen, chlorine, bromine or $C_{1-6}$alkyl, Z is —$CR_4$= wherein $R_4$ is hydrogen, $C_{1-6}$-alkyl, chlorine or bromine, A is —$CR_7$= wherein $R_7$ is hydrogen or $C_{1-6}$alkyl, preferably those wherein B is a radical of formula (b), $R'_{10}$ being $C_{1-12}$alkyl or $C_{1-6}$alkyl substituted by NH—CO—phenyl or benzimidazolyl, have e.g. an antagonist effect on central 5HT-1C receptors and are therefore useful in the prophylactic treatment of migraine and in the treatment of psychiatric disorders e.g. anxiety, obsessive compulsive disorders, opanic attacks, depression or bulimia. Compound of Example 38 is preferred.

Compounds of formula I wherein $R_5$ is hydrogen, hydroxy, $C_{1-6}$alkoxy, carboxy, $C_{2-6}$alkoxycarbonyl, CON$R_aR_b$, $SO_2NH(C_{1-6}$alkyl), $C_{1-6}$alkyl substituted by $SO_2C_{1-6}$alkyl, or PO($C_{1-4}$alkyl)$_2$, W is NH, A is —CH=, Z is —CH= and $R_2$ and $R_6$ are each hydrogen, particularly those wherein B is a radical

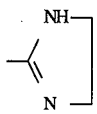

or a radical (b) wherein $X_2$ is $C_{1-12}$alkyl or —CONH—$C_6H_{11}$, have e.g. an agonist effect on 5HT-1D receptors and are therefore useful in treating conditions associated with cephalic pain, e.g. as indicated above. Compound of Example 63 is particularly preferred.

We claim:

1. A compound of the formula

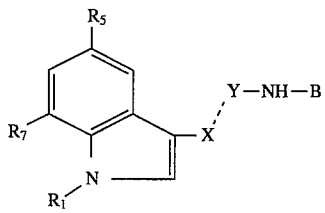

wherein $R_1$ hydrogen; $C_{1-6}$alkyl; ($C_{1-6}$alkyl)carbonyl; or benzoyl;

$R_5$ is hydrogen; halo; $C_{1-6}$alkyl; hydroxy; nitro; amino; $C_{1-4}$alkylamino; $C_{1-10}$alkylcarbonylamino; $C_{2-6}$alkoxy-carbonyl; $SO_2NR_aR_b$; cyano; trimethylsilyl; $C_{1-6}$alkyl monosubstituted by —$SO_2$-($C_{1-6}$alkyl), —$SO_2NR_aR_b$, —$CONR_aR_b$, —NH—$SO_2$—($C_{1-6}$alkyl), —N ($C_{1-6}$alkyl)—$SO_2$— ($C_{1-6}$alkyl), —$NR_aR_b$, $C_{2-6}$alkoxycarbonyl or —PO($C_{1-4}$alkyl)$_2$; carboxy; $CONR_aR_b$; —PO($C_{1-4}$alkyl)$_2$;
—$OCONR_cR_d$; $C_{1-6}$alkoxy; $C_{1-6}$alkoxy monosubstituted by hydroxy, $C_{1-4}$alkoxy, $NR_aR'_b$, $CONR_aR_b$, CSN$R_aR_b$, ($C_{1-6}$alkyl)carbonyloxy or benzoyloxy; $C_{2-6}$alkenyloxy; pyridyl-carbonyloxy; ($C_{1-6}$alkyl)carbonyloxy; or benzoyloxy;

and wherever they appear in the above definition of $R_5$, each of $R_a$ and $R_b$, independently, is hydrogen or $C_{1-6}$alkyl; $R'_b$ is hydrogen or $C_{1-6}$alkyl; and each of $R_c$ and $R_d$, independently, is $C_{1-6}$alkyl;

$R_7$ is hydrogen, halo, $C_{1-6}$alkyl or $C_{1-6}$alkoxy;

X—Y is —$CR_8$=N— or —H($R_8$)—NH— where $R_8$ is hydrogen or $C_{1-6}$alkyl; and B is a radical of formula (a) or (b),

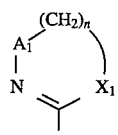

where n is 1 or 2;

$A_1$ is C=O or $CH_2$;

$X_1$ is S; $NR_{11}$ where $R_{11}$ is hydrogen; or $CR_{12}R_{13}$ where each of $R_{12}$ and $R_{13}$, independently, is hydrogen or $C_{1-4}$alkyl;

$R_{10}$ is hydrogen; $C_{1-12}$alkyl; $C_{1-6}$alkyl monosubstituted by hydroxy, aryl, aryloxy, adamantyl, a heterocyclic radical, —NH—$SO_2$-aryl or —$NR_{15}$—$COR_{16}$ where $R_{15}$ is hydrogen or $C_{1-4}$alkyl and $R_{16}$ is $C_{1-6}$alkyl, $C_{5-7}$cycloalkyl, $C_{5-7}$cycloalkyl-$C_{1-4}$alkyl, aryl or aryl($C_{1-4}$alkyl); $C_{5-7}$cycloalkyl; adamantyl; ($C_{1-10}$alkyl)-carbonyl; benzoyl; phenyl($C_{1-4}$alkyl)carbonyl; or —$CONHR_{14}$ where $R_{14}$ is $C_{1-10}$alkyl or $C_{5-7}$cycloalkyl;

and wherever "aryl" appears as is or in the significances "aryloxy", "—NH—$SO_2$-aryl" or "aryl($C_{1-4}$alkyl)" in the above definition, it is phenyl or phenyl mono- or disubstituted by fluoro, chloro, methyl or methoxy; and wherever the term "a heterocyclic radical" appears in the above definition, it is pyridyl, imidazolyl, benzimidazolyl, pyrrolidinyl, piperidino, pyrazinyl, perhydroindolyl or a radical of formula (d)

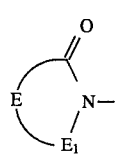

where

E is —$CH_2CH_2$—, —$CH_2N(R_{17})$— where $R_{17}$ is hydrogen or $C_{1-4}$alkyl; or —($CH_2)_3$— where one or two hydrogens therein can be replaced by $C_{1-6}$alkyl; and $E_1$ is —CO— or —$CH_2$—;

and $X_2$ is —$SR_{20}$ where $R_{20}$ is $C_{1-6}$alkyl; or —$NR_3R'_{10}$ where either $R_3$ is hydrogen or $C_{1-6}$alkyl and $R'_{10}$ has one of the significances indicated above for $R_{10}$; or $R_3$ and $R'_{10}$ together with the nitrogen atom to which they are attached form a heterocyclic radical as defined above; with the proviso that where B is a radical of formula (b), only one of $R_{10}$ and $R'_{10}$ can be other than hydrogen and $X_2$ can be —$SR_{20}$ only when $R_{10}$ is hydrogen; which compound is in free base or pharmaceutically acceptable salt form.

2. A compound of claim 1 wherein each of $R_1$ and $R_7$ is hydrogen.

3. A compound of claim 1 wherein each of $R_1$ and $R_7$ is hydrogen and $R_5$ is hydroxy or $C_{1-6}$alkoxy.

4. A compound of claim 1 wherein at least one of $R_1$ and $R_7$ is other than hydrogen.

5. A compound of claim 1 wherein each of $R_1$ and $R_7$ is hydrogen and $R_5$ is hydrogen, hydroxy, $C_{1-6}$alkoxy, carboxy, $C_{2-6}$alkoxycarbonyl, $CONR_aR_b$ where $R_a$ and $R_b$ are as defined in claim 14, $SO_2NH(C_{1-6}$alkyl) or $C_{1-6}$alkyl monosubstituted by —$SO_2$— ($C_{1-6}$alkyl) or —$PO(C_{1-4}$alkyl)$_2$.

6. A compound according to claim 1 which is 5-methoxy-indole-3-carboxaldehyde amino-(pentyl-amino)methylene-hydrazone, in free base form or in pharmaceutically acceptable salt form.

7. A compound according to claim 1 which is [5-hydroxy-indole- 3-carboxaldehydeamino(N-cyclo-hexylureido)methylenehydrazone, 5hydroxy-indole- 3-carboxaldehyde amino (3-benzimidazol-2-yl-propylamino)methylenehydrazone] 5-carbamoyl-indole-3-carboxaldehydeamino(pentyl-amino)methylenehydrazone, 5-hydroxy-7-methyl-indole-3-carboxaldehyde amino(pentyl-amino)methylene-hydrazone, 1-ethyl-5-hydroxy-indole-3-carboxaldehyde amino (pentyl-amino)methylenehydrazone and 5-hydroxy-7-methyl-indole-3-carboxaldehyde amino (N-methyl-N-pentyl-amino)-methylenehydrazone, all of which are in free base form or in pharmaceutically acceptable salt form.

8. A pharmaceutical composition comprising a pharmaceutically acceptable carrier or diluent and a therapeutically effective amount of a compound of claim 1, which compound is in free base or pharmaceutically acceptable salt form.

9. A method of treating a gastrointestinal motility disorder comprising administering to a subject in need of such treatment a therapeutically effective amount of a compound of claim 1, which compound is in free base or pharmaceutically acceptable salt form.

10. A method according to claim 9 wherein the disorder is irritable bowel syndrome, gastroesophageal reflux disease or constipation.

11. A method of treating a disorder associated with cephalic pain comprising administering to a subject in need of such treatment a therapeutically effective amount of a compound of claim 1, which compound is in free base or pharmaceutically acceptable salt form.

12. A method according to claim 11 wherein the disorder is migraine headaches.

13. A compound of claim 1 wherein B is a radical

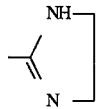

or a radical of formula (b) where $R_{10}$ and $X_2$ are as defined in claim 1.

14. The compound of claim 6 which is in pharmaceutically acceptable acid addition salt form.

15. The compound of claim 6 which is in hydrogen maleate form.

16. A compound according to claim 1 where X--Y is —$CR_8$=N—.

17. A compound according to claim 1 where B is a radical of formula (b) where $R_{10}$ is hydrogen and $X_2$ is —$NR_3R'_{10}$ where $R_3$ is hydrogen or $C_{1-4}$alkyl and $R'_{10}$ is $C_{1-12}$ alkyl.

* * * * *